United States Patent [19]

Monroe et al.

[11] Patent Number: 5,311,859
[45] Date of Patent: May 17, 1994

[54] ADD-ON VIDEO CAMERA ARRANGEMENT FOR OPTICAL LAPAROSCOPE

[75] Inventors: Richard A. Monroe, Liverpool; Robert J. Wood, Syracuse, both of N.Y.

[73] Assignee: Welch Allyn, Inc., Skaneateles Falls, N.Y.

[21] Appl. No.: 943,931

[22] Filed: Sep. 11, 1992

[51] Int. Cl.$^5$ .................................. A61B 1/06
[52] U.S. Cl. .................................. 126/6; 354/62; 348/75
[58] Field of Search ................. 128/6; 358/98; 354/62

[56] References Cited

U.S. PATENT DOCUMENTS

| | | | |
|---|---|---|---|
| 4,611,888 | 9/1986 | Prenovitz et al. | 128/6 X |
| 4,851,866 | 7/1989 | Ciarlei et al. | 358/98 X |
| 4,855,819 | 8/1989 | Hibino et al. | 358/98 |

Primary Examiner—Richard J. Apley
Assistant Examiner—Beverly A. Meindl
Attorney, Agent, or Firm—Harris Beach & Wilcox

[57] ABSTRACT

An add-on video camera arrangement permits onscreen viewing of a target within an enclosed structure, such as a patient's body cavity, using an optical laparoscope. A standard C-mount adaptor is fitted to the ocular of the laparoscope lens tube. The camera arrangement has a handle unit that is formed of a short one piece housing. A camera lens and imager unit is disposed therein at the distal end of the housing. A standard female-thread socket receives the standard male thread of the C-mount adaptor. A flexible umbilical tube couples the housing to a connector module that plugs into a light and power supply unit. The fiber optic bundle light conduit has its proximal end within the connector module to receive light from the light unit, and the light conduit extends through the umbilical tube in the handle unit housing and exits the housing at a light conduit port. A flexible tubular connector extends from this port and carries the fiber optic bundle light conduit. A coupler device at the distal end of this conduit fits onto the light tube fitting that is provided on the laparoscope lens tube.

8 Claims, 2 Drawing Sheets

ADD-ON VIDEO CAMERA ARRANGEMENT FOR OPTICAL LAPAROSCOPE

BACKGROUND OF THE INVENTION:

This invention relates generally to borescopes or endoscopes of the type in which a video camera is mounted onto an elongated insertion tube which carries an image of a target that is concealed within an enclosure, i.e. the body cavity of a human patient. The invention is more particularly concerned with an add-on camera for an optical laparoscope which produces a video image of the target for display on a video monitor.

Recently, interest has increased in the use of video instruments for surgical applications to permit a surgeon to carry out a procedure with minimal intervention in the patient. An example of one such video instrument is a laparoscope for performing surgery in the abdominal cavity, where the instrument is inserted through a small incision. Other probes are provided for diagnosis of medical conditions in the colon or in the gastro-enteric tract. Small probes can also be used in eye surgery. Further examples are found in industrial probes, i.e., borescopes, for inspection of equipment such as boilers or steam generators, or of jet engine rotors where nondestructive penetration of the equipment is necessary.

Most commonly, a laparoscope employs a lens tube which acquires an image in an objective lens at its distal end, a relay lens system within the lens tube, and an ocular or eyepiece at the proximal end which permits viewing of tissues within the patient's body cavity.

In order to illuminate target body tissues, light is carried on optical fibers within the lens tube. A fitting at or near the proximal end of the lens tube contains one end of a fiber optic bundle, and couples to a flexible light conduit that in turn receives light from a light source. The fiber optic bundle fans out inside the lens tube and the fibers terminate at the distal or objective end.

A C-mount adapter is employed with a laparoscope to couple the eyepiece to a camera for observing the tissues on screen or for recording the image electronically or on film. The adapter has a fitting on its distal end for attaching to the laparoscope eyepiece, a standard malethread fitting on its proximal end for screw mounting to a camera, and a lens system for focusing and adjusting the image of the target.

Up until this time, camera attachments for optical laparoscope have been heavy and clumsy to use, and have require a separate light box for the illumination conduit and video processor and power supply for the camera. Also, up until now light sources for probes of this type have produced high levels of infrared, i.e., radiant heat, as well as visible radiation. The infrared causes a danger of tissue damage from heating. This limits the flexibility of laparoscopic procedures and limits the amount of time that any individual organ or tissue cluster can be observed.

Recently, a laparoscopic instrument has been proposed in which a small video camera is carried at the distal end of a rigid insertion tube, and a balanced white light is produced by a low-power metal halide discharge lamp which produces red, green, and blue visible light but only a minimal amount of infrared so that the danger of tissue damage is reduced. A device of this type is described in U.S. patent application Ser. No. 07/780,762, filed Oct. 22, 1991, and having a common assignee herewith.

In this type of instrument, the insertion tube is connected by a flexible cable or umbilical to a connector module that plugs into a socket in a light and power supply unit. A video cable that extends through the insertion tube and umbilical has terminals in the connector module that supply the video signal from the miniature camera to a wiring harness in the light and power supply unit, which supplies a suitable signal to a full color or monochrome monitor. An image of a target area, such as a tissue within an patient's body cavity, can be viewed on the monitor.

Also within the light and power supply unit is a high illuminance, but low-wattage light source in the form of one or more metal halide discharge lamps. These can preferably be of the type described in copending U.S. patent applications Ser. Nos. 07/484,166, filed Feb. 23, 1990; 07/636,742, 07/636,743, and 07/636,744, each filed Dec. 31, 1990, and which have an assignee common herewith. The lamp typically operates at a power of about 20 watts, and has an efficacy of 35 lumens per watt or more. The quality of light produced, which can be controlled by the selection of salts employed, the dosage of mercury, and mechanical structure, has an emission spectrum in the visible band, with very little radiation produced in the infrared band. Also, the arc gap of this lamp is small, which produces a small spot of light when focused onto the fiber optic bundle used for illumination. The small spot size allows almost all the light energy to be directed into the proximal end of a very small fiber bundle. The small illumination bundle permits the insertion tube to be made much smaller than was otherwise possible while still delivering plenty of light to the target area. Also, because small optical fiber bundles can be used, the probe can incorporate redundant optical fiber bundles which can each be associated with a respective light source. Moreover, because the lamp operates at low power (e.g. 20 watts), producing limited infrared radiation, and because virtually all the light is focused onto the fiber optic bundle, the light source can be made much more compact. Also, the lamp ballast and power supply can be made much smaller and easier to cool.

The light incident on the target contains substantially only visible light, with very little radiant heat. This permits the operator to view and examine tissues for extended intervals without danger of tissue damage.

The modular connector at the proximal end of the umbilical tube permits the instrument to be plugged into the socket of the light and power unit, or unplugged and then inserted in another similar unit as need be. Also, a number of instruments of similar or different styles, but with similar modular connectors, can be used interchangeably with one or another of the light and power units.

No one until now has made or proposed a video camera attachment for attaching to the eyepiece of a traditional optical laparoscope lens tube, and which can be quickly plugged into a light and power unit.

SUMMARY OF THE INVENTION

It is an object of this invention to provide an improved add-on camera arrangement for a laparoscope that avoids the problems of the prior art.

It is another object to provide a convenient, well-balanced camera assembly which is convenient to handle and manipulate, and which provides convenient coupling of the light conduit fitting of the optical laparoscope lens tube.

In accordance with an aspect of this invention, an add-on video camera arrangements permits on-screen viewing of an obscured target, such as a body tissue within a patient's body cavity, using a traditional optical laparoscope, in which a C-mount adaptor is positioned on the ocular of the laparoscope lens tube. The add-on camera arrangement has a handle portion with a short housing having a hollow interior. There is a CCD imager mounted within the housing with a lens imager assembly positioned at the housing distal end, where a female standard thread receives the male standard thread of the C-mount adaptor. A flexible umbilical tube connects the proximal or rear end of the handle housing to a connector module that fits removably into a socket of a light and power unit. Inside this module, the video processing of the CCD imager occurs.

When coupled to the optical laparoscope the add-on arrangement is convenient for the surgeon or other practitioner to manipulate. Its single umbilical containing both the illuminating fibers and the video electronic signal conductors and coupled to the associated light and power supply unit avoids clutter and minimizes confusion during a surgical procedure. The add-on camera arrangement can be employed with large or small probes, including flexible endoscopes, e.g. for abdominal surgery or for arthroscopic procedures.

The above and many other objects, features and advantages of this invention will become apparent from the ensuing description of a preferred embodiment, to be read in conjunction with the accompanying Drawing.

DETAILED DESCRIPTION OF THE PREFERRED EMBODIMENT

Figure 1:
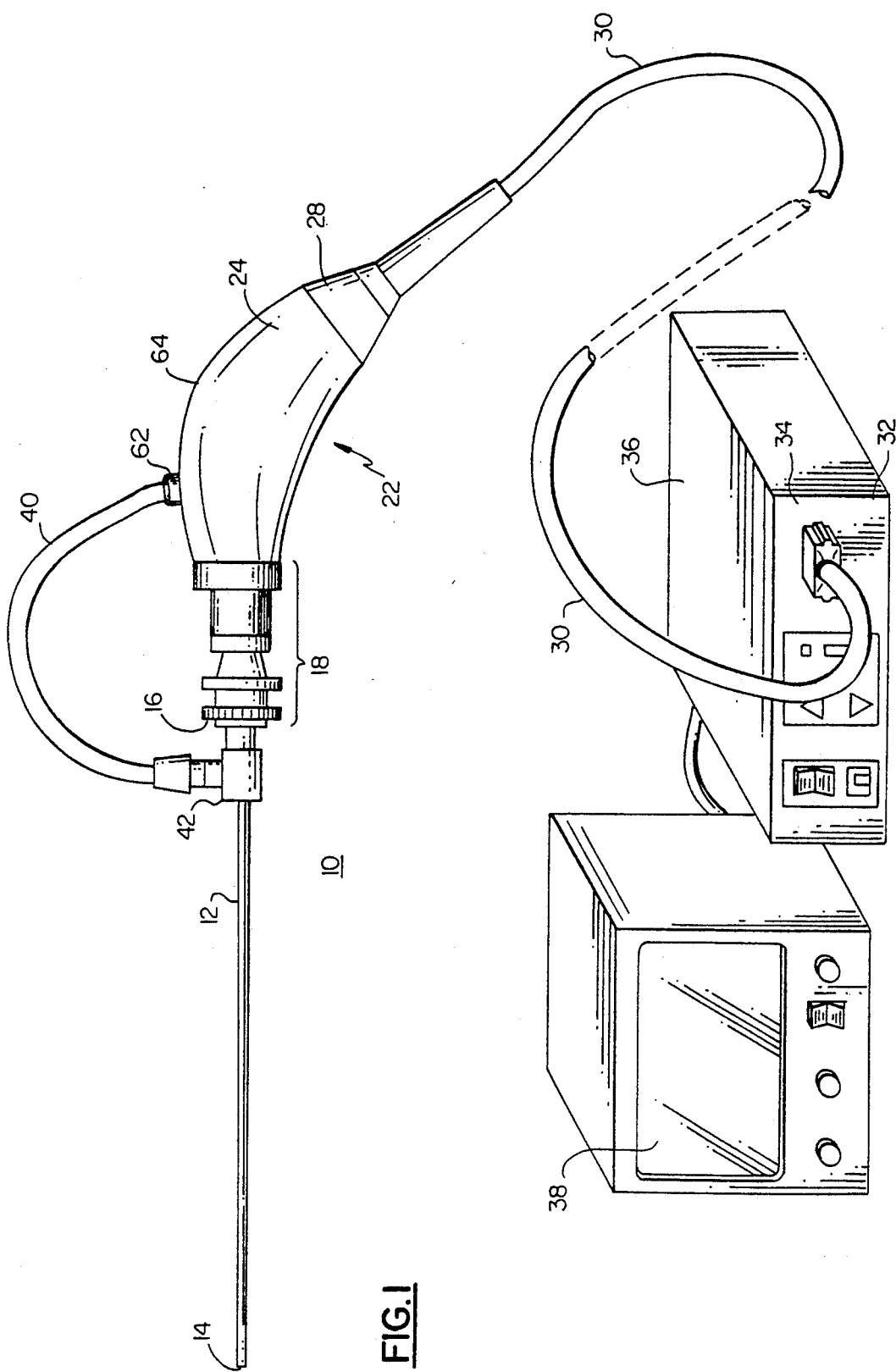
FIG. 1 is a perspective view of an add-on camera arrangement for an optical laparoscope, according to one embodiment of the invention.

With reference to the Drawing and initially to FIG. 1, a typical laparoscope instrument 10 is shown to comprise an elongated rigid lens tube 12 with an objective 14 at its distal end, which is inserted into a patient, and an eyepiece or ocular 16 at the proximal end. Here, a standard C-mount adapter 18 is fitted onto the ocular 16. The C-mount adapter 18, as is standard, has a distal end that adjusts to fit the eyepiece 16, a proximal end with a standard male thread, and a group of lenses for adjustably focusing the image that is carried by the lens tube 12.

An add-on camera assembly 20 according to one embodiment of this invention has a handle portion 22, formed of a single housing 24 and a proximal threaded coupler 28 that joins a flexible tubular umbilical 30 to the handle. This umbilical 30 carries signal and power conductors and also carries a fiber optic illumination bundle between the handle 22 and a plug-in modular connector 32. The structure of the connector 32 is described in commonly-assigned copending U.S. patent application Ser. Nos. 07/780,762 filed Oct. 22, 1992 and 07/944,221 filed Sep. 11, 1992.

The modular connector 32 is removably inserted into a socket 34 in a power and light supply unit 36. This unit contains a power supply which furnishes suitable power levels for the assembly, and also contains a suitable light source providing, e.g., white light. Preferably, a low-wattage metal halide discharge lamp is employed, so that the light that is produced contains principally visible red, white and blue wavelengths, but relatively little radiation of the infrared radiant heat wavelengths.

A wiring bundle within the unit 36 carries video signals which are then supplied to an associated video monitor 38. The latter can be a color or black-and-white CRT, a flat-screen monitor, a projection monitor, or other viewing device, as desired.

As also shown in FIG. 1, a flexible light conduit 40 connects between the housing 24 of the handle 22 and a light conduit fitting 42 on the laparoscope lens tube 12. This carries the fiber optic bundle to the lens tube and provides the light which is then carried through a successive fiber optic bundle within the lens tube 12, which illuminates a target within the viewing area of the objective 14.

Figure 2:
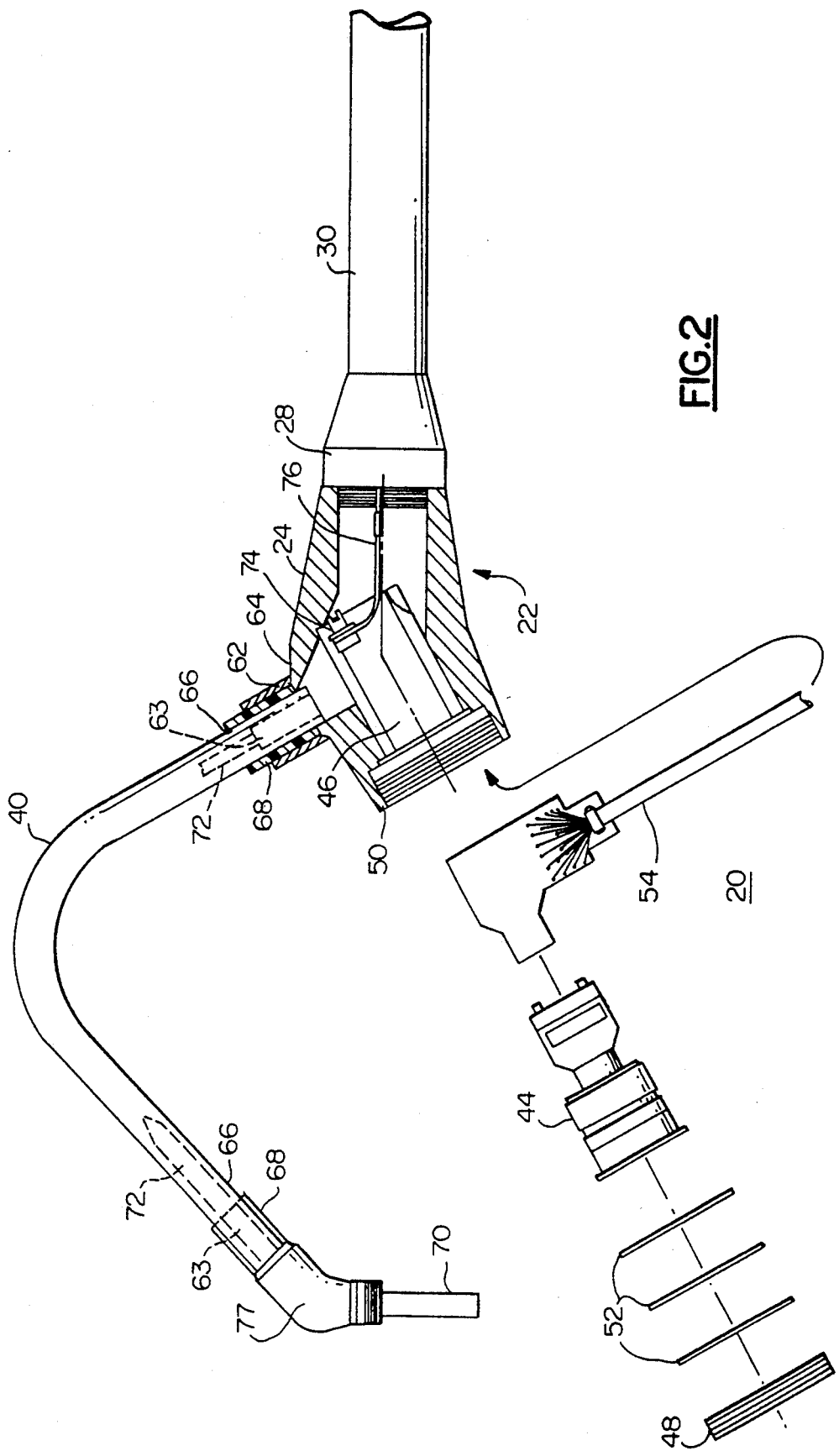
FIG. 2 is a sectional view showing a portion of the add-on camera arrangement of FIG. 1

As shown in more detail in FIG. 2, a video camera lens and imager module 44 is disposed within a cavity 46 or void inside the housing 24. At the very distal end of the housing 24 is a female threaded socket 48 with a standard thread to fit a standard male thread of the C-mounted adapter 18. The threaded socket 28 is in the form of a threaded ring which fits a threaded receptacle 50 in the distal end of the housing 24. Several retaining rings 52 hold the imager module 44 behind the socket or threaded ring 48.

The lens and imager module 44 is mounted through a flexible coupling circuit 54 that contains filters and clock shaping electronics. A video processing unit (not shown) is mounted in the interface module connected to this imager through a standard or nominal length of cable. Within this module are the video electronics output encoders/drivers and cable length compensation circuits.

A rigid tubular tunnel 62 exits the front portion 24 of the housing just ahead of a bend 64, so that the tunnel 62 is oriented somewhat forwards. A rigid stem 63 is threaded into the tunnel 62 of the housing 24. A flexible boot 68 is slid over the flexible sheath 66 and then seated into the tunnel 62. Another rigid stem 63 is threaded into the connector 75. Another flexible boot 68 is slid over the other end of the flexible sheath 66 and is then seated into a connector 77. At the distal end, a ferrule 70 receives the distal end of a fiber optic bundle 72 and holds the same against the light guide fitting 42 of the lens tube 12. A number of different fiber optic adapters can be added to the coupler in order to mate with the many different laparoscope fiber optic couplers which are current available. At the bend 64, the distal portion 24 is angulated a desired amount, preferably by 30 to 45 degrees.

The fiber optic bundle 72 extends proximally from the ferrule 70 through the sheath 66 and tunnel 62 into the interior of the handle 22. From there the bundle 70 extends proximally through the umbilical tube 30 to the modular connector 32. As mentioned earlier, the proximal end of the fiber optic bundle 72 is disposed at the source of illumination, e.g. a focussed spot generated by a metal halide discharge lamp.

A grounding screw 74 and grounding strap 76 are shown within the housing 24. The strap 76 extends proximally to the modular connector 32.

Preferably, the entire add-on camera assembly 20, including the handle portion 22, the flexible light conduit 40, the umbilical 30, and the plug-in modular connector 32 are environmentally sealed, and contain dry nitrogen or another suitable inert gas at a pressure over ambient. The entire unit is sterilizable by immersion into a liquid or gas sterilizing agent, such as ethylene oxide. Because of the standard thread 48 in the handle unit 22, which receives a standard C-mount adaptor, the add-on camera assembly can be employed with any standard optical laparoscope. Thus, on-screen viewing can be achieved with this either with very narrow needle type probes, e.g. with rod lens optics, and with laparoscope with intermediate or larger diameter lens tubes, containing discrete lens relay systems.

The add-on camera of this system can be used interchangeably with probes of the type having distally mounted video camera, but employing a similar light and power supply unit 36. This system provides sufficient visible illumination for superior viewing without significant amount of radiant heat. The single umbilical 30, which carries both the illumination fiberoptic bundle and also video signal conductors, avoids problems of clutter and confusion for the physician. While not shown here, there are grounding conduits and other suitable protective means to ensure that the patient receives no electrical discharge from the unit. As shown here, the housing upper unit 24 is angulated or bent at about 30 to 45 degrees for convenient handling, but without sharp angles or corners. Other embodiments could have other amounts of angulation. The light conduit 40, is sufficiently long to permit the rotation of the light tube CW 12, over about 90°, but is short enough so that the loop that it forms does not contact the patient during a procedure.

With the add-on camera arrangement of this invention, a high-quality video image of the target is displayed for viewing on a monitor, using a conventional optical laparoscope. The add-on assembly is convenient and light in weight, simple to use and to clean for subsequent use. The housing unit 24, and the coupler 28 are formed of lightweight durable materials, such as aluminum.

While this invention has been described in detail with reference to a preferred embodiment, it should be understood that the invention is not limited to that precise embodiment. Rather many modifications and variations will present themselves to those of skill in the art without departing from the scope and spirit of this invention, as defined in the appended claims.

What is claimed is:

1. Add-on video camera arrangement to permit on-screen viewing of a target within an enclosed structure using an optical laparoscope of the type comprising an elongated insertion tube containing optical means for conducting an optical image of the target from an objective at a distal end of the insertion tube to an ocular at a proximal end thereof, and light conduit means therein for conducting illumination for a proximal light tube fitting to said distal end of the insertion tube to illuminate said target; and a C-mount adaptor which includes a distal end fitting said ocular, a proximal end having a standard male thread for fitting to a camera, and internal focussing means for adjustably focusing the image of said target; said add-on camera arrangement comprising:
    a handle unit including an elongated housing having a hollow interior with a camera lens and imager assembly disposed therein, a distal end thereof having a socket with a standard female thread to receive the standard male thread of said adapter; and a light conduit port exiting said housing;
    a flexible umbilical tube coupled to said housing and to a connector module and containing conductors for carrying power to said camera lens and imager assembly and conducting therefrom a video signal, said connector module insertably fitting a socket of a light unit which contains a light source;
    a fiber optic bundle light conduit having a proximal end carried in said connector module to receive light from said light source, and extending through said umbilical tube and said handle unit housing and exiting said light conduit port; and
    a flexible tubular connector extending from said light conduit port and carrying said fiber optic bundle light conduit, and including a coupler device at a distal end of the conduit, in which a distal end of said fiber optic bundle light conduit is disposed, for engaging onto said light tube fitting, such that the flexible tubular connector forms a short loop, from the handle unit to the light tube fitting of the insertion tube, that is sufficiently long to permit rotation of the insertion tube relative to the handle over at least 90 degrees but is short enough so that the loop does not contact the structure being inspected during a procedure.

2. Add-on camera arrangement according to claim 1 wherein said handle housing has said imager assembly located distally within the housing.

3. Add-on camera arrangement according to claim 2 wherein a rigid coupler threadably mounted onto a threaded union member disposed at the proximal end of said handle unit joins said umbilical tube thereto.

4. Add-on camera arrangement according to claim 1 wherein said handle housing is angulated to include a bend of an angle of about 30 to 45 degrees, but is not limited to these angles and may be flexible in construction.

5. Add-on camera arrangement according to claim 4 wherein said light conduit port is disposed distally of said bend on said proximal portion of said housing.

6. Add-on camera arrangement according to claim 5 wherein said light conduit port includes a rigid tubular member projecting from said handle housing.

7. Add-on camera arrangement according to claim 1 further comprising a camera processor element situated within said connector module and cabling means for electrically coupling the camera lens and imager assembly with the camera processor element located within said module.

8. Add-on camera arrangement according to claim 2 wherein said handle unit housing is formed of aluminum.

* * * * *